United States Patent [19]

Costello

[11] Patent Number: 4,901,141
[45] Date of Patent: Feb. 13, 1990

[54] FIBEROPTIC DISPLAY FOR A VIDEO IMAGE

[75] Inventor: James G. Costello, Huntington Beach, Calif.

[73] Assignee: Olympus Corporation, Lake Success, N.Y.

[21] Appl. No.: 279,770

[22] Filed: Dec. 5, 1988

[51] Int. Cl.⁴ .............................................. H04N 7/18
[52] U.S. Cl. .................................. 358/93; 128/653 A; 324/318; 358/901; 350/96.25
[58] Field of Search ................... 358/901, 93; 324/318, 324/319, 320; 128/653 R, 653 A, 653 AF, 653 SC; 350/96.25

[56] References Cited

U.S. PATENT DOCUMENTS

| | | | |
|---|---|---|---|
| 3,142,235 | 10/1960 | Siegmund . | |
| 3,712,714 | 6/1971 | Uyeda et al. | 350/301 |
| 3,748,016 | 7/1973 | Rossire | 358/901 |
| 3,809,908 | 5/1974 | Clanton | 358/901 |
| 3,833,300 | 5/1974 | Rymes | 356/13 |
| 3,945,716 | 12/1974 | Kinder | 350/174 |
| 4,032,970 | 7/1976 | Anderson | 358/93 |
| 4,090,104 | 3/1977 | Vann et al. | 358/901 |
| 4,651,099 | 3/1987 | Vinegar | 324/320 |
| 4,689,565 | 8/1987 | Kemner | 324/318 |
| 4,694,837 | 8/1985 | Blakeley et al. | 128/653 |
| 4,719,424 | 8/1986 | Jimbo et al. | 324/309 |
| 4,727,882 | 4/1986 | Schneider et al. | 128/653 |
| 4,728,890 | 6/1986 | Pattany et al. | 324/309 |
| 4,730,620 | 7/1987 | Bailes | 128/653 |
| 4,742,389 | 2/1987 | Schiffman | 358/250 |
| 4,761,613 | 8/1987 | Hinks | 324/309 |

OTHER PUBLICATIONS

MOS-III advertising literature and Clinical Studies Results.

Primary Examiner—Howard W. Britton
Attorney, Agent, or Firm—Kenyon & Kenyon

[57] ABSTRACT

A coherent fiberoptic display for a region having strong magnetic field. Transfer optics launch the image into one end of a coherent fiberoptic bundle that transfers the image to the display. Transfer optics at the other end of the coherent fiberoptic bundle direct the image to a fiberoptic taper. The image is viewed on the expanded end of the fiberoptic taper. The image can comprise a video image formed by a CRT located in a region of low magnetic flux density and the fiberoptic taper can be positioned in the imaging zone of a Magnetic Resonance Imaging (MRI) apparatus. The video image can allow the patient to watch television during magnetic resonance imaging. This distraction will reduce the anxiety experienced during magnetic resonance so that the patient is less apt to move and the magnetic resonance images are less apt to be blurred or destroyed. The efficiency of magnetic resonance imaging is thus improved.

22 Claims, 2 Drawing Sheets

FIBEROPTIC DISPLAY FOR A VIDEO IMAGE

BACKGROUND OF THE INVENTION

The present invention relates to a fiberoptic display for displaying an image in a region having a strong magnetic field. A coherent fiberoptic bundle transfers the image across a gradient between regions having different magnetic flux densities. The present invention is particularly well suited for transferring a video image from a cathode ray tube (CRT) to a fiberoptic display scope positioned in the imaging zone of a magnetic resonance imaging (MRI) system.

The image transfer system for the fiberoptic display of the present invention applies to transferring any optical image across the gradient between a region of high magnetic flux density and a region of low magnetic flux density. The invention will be illustrated through application to the problem of projecting a video image into the imaging zone of an MRI system.

Magnetic resonance imaging is a well known process that creates a three dimensional image of the distribution of magnetic dipoles in a body. The resulting images can be used to make medical diagnosis. The process involves positioning the patient in an imaging zone of a MRI apparatus for approximately 40 minutes. The MRI apparatus generates a strong magnetic field around the patient to create a region having a high magnetic flux density. This magnetic field is systematically changed so as to change the orientation of the dipoles in the patient. The three dimensional image is constructed from measurements made of the changes the orientations of the dipoles.

The art recognizes that the resolution obtained using magnetic resonance imaging is degraded or destroyed if the patient moves during the imaging process. Motion can result from the normal functioning of the patient's respiratory and cardiovascular system. Furthermore, the process of making a magnetic resonance image causes anxiety. The patient must be placed in the confined space of the imaging zone of an MRI apparatus which can induce feelings of claustrophobia. The MRI apparatus itself is shielded from its surroundings to attenuate the magnetic field. The shielding further isolates the patient in the imaging zone. The MRI apparatus makes a noise during the imaging process that is similar to a power transformer. Some say that such a strong magnetic field is perceptible and produces a strange sensation. The extended confinement, unfamiliar surroundings and sensations can create anxiety—particularly for children. A natural response to anxiety is nervous behavior such as twitching or fidgeting. This motion causes a physical displacement of the patient that can blur and destroy the magnetic resonance image. The imagining process must then be lengthened or repeated which can create even more anxiety.

It is recognized in the art that patient motion can blur or destroy a magnetic resonance image. Electronic systems have been used to compensate for motion by modifying the way that the magnetic resonance image is formed. These electronic systems often seek to eliminate the effects of respiratory or cardiovascular functions by exploiting their periodic motion. The effects of motion caused by the physical displacement of the patient, however, are far more difficult to eliminate with electronic systems because this type of motion is not predictable. The electronics needed to compensate for the physical displacement of a patient needs to be highly complex and therefore also quite expensive.

It is known in the art that anxiety can be reduced by distracting the patient with a television. A person who is distracted by a familiar show is less frightened by confined surroundings and strange sensations.

While these general principles are known, their application to magnetic resonance imaging is not simple. For example, the CRT used to create a video image in a television would not function in the strong magnetic field created in the imaging zone of the MIR system and may be disturbed outside the shield by any magnetic flux that leaks out. A CRT forms an image by scanning an electron beam across the phosphor screen that forms the back side of the display screen. The electron beam is scanned by deflecting it with magnets. The beam can be disturbed or totally overwhelmed or by the magnetic field created during magnetic resonance imaging. The electron beam of a CRT would not be able to scan the phosphor screen in a region of high magnetic flux density. A CRT therefore could not produce an image in the imaging zone during magnetic resonance imaging.

The image formed by a solid state display of liquid crystal diodes (LCD's) also could be disturbed by the high magnetic flux density. Any electric current induces a magnetic field that will interact with any other magnetic field nearby. The electric signals used to control a solid state display could therefore be destroyed by interaction with the magnetic field in the imaging zone of an MRI system. The systematic changes in the magnetic LCD field would make a display even less practical.

The electrical signals needed to generate any video signal would likely disturb the magnetic resonance image. The induced field from a video display could be stronger than the dipoles of the atoms and molecules that the MRI system is designed to measure. The resulting disruptions would be difficult to eliminate.

The only way thus far proposed to communicate with a patient undergoing magnetic resonance imaging is to supply sound to the imaging zone using an air hose system similar to that used to supply music to the passengers on many aircraft. The air hose system avoids the problem of transferring an electromagnetic signal into the imaging zone of an MRI system by transferring the music through air rather than through a wire. Sound is not an electromagnetic signal and is therefore not effected by high magnetic flux density.

The need to eliminate the adverse effects on the magnetic resonance image caused by the motion of the patient have been addressed by electronic systems that reduce the effects of image blurring. No system other than sound delivered by air hoses is known that could communicate with a patient during magnetic resonance imaging. One solution that has been attempted is to equip the patient with glasses made of a magnetically inert material to reflect a scene from outside the imaging zone into the field of view of the patent. Clinical tests have shown that these glasses are effective in easing anxiety in patients prone to claustrophöbia. The glasses, however, are not known to project a moving image to a patient and therefore do not provide an active distraction to relieve more general feelings of anxiety.

A need exists in the art to reduce the tendency of a patient to move while undergoing magnetic resonance imaging by displaying a video image in the measuring area of an MRI system to distract the patient and thus increase the efficiency of the magnetic resonance image by reducing the number of scans that must be redone.

SUMMARY OF THE INVENTION

The present invention provides a method and apparatus for transferring an optical image between regions having high and low magnetic flux densities across the intervening magnetic flux gradient. Transfer optics can launch the video image formed in one region into a coherent fiberoptic bundle that transfers the optical image across the magnetic flux gradient into the other region. Additional transfer optics then transfer the optical image to a display such as a fiberoptic taper.

The method and apparatus of the present invention provide for increasing the efficiency of a magnetic resonance imaging apparatus by distracting the patient with a video image so as to lessen anxiety and reduce his or her tendency to move. The invention forms the video image in a region of low magnetic flux density and then transfers the image into the region having a high magnetic flux density using light to transfer the video image.

Forming the video image in the region of low magnetic flux density encounters none of the difficulties associated with forming the image in a region having a high magnetic flux density. Transferring the video image into the imaging zone is easy to do using known image transfer techniques. The video images are conveyed by light which is a type of electromagnetic radiation that experiences no significant interaction with a strong magnetic field. The present invention can thus transfer a video image to the imaging zone of the MRI system despite the high magnetic flux density present during magnetic resonance imaging.

The present invention can use a coherent fiberoptic bundle to transfer a video image into the region of high magnetic flux density in the imaging zone. Transfer optics launch the image of a high intensity CRT screen into one end of the coherent fiberoptic bundle that extends across a magnetic flux gradient such as that formed by the shielding that surrounds a MRI system. Transfer optics at the other end of the coherent fiberoptic bundle direct the video image to a fiberoptic taper. The patient views the video image on the expanded end of the fiberoptic taper. The video image can combine with sound to allow the patient to watch television during magnetic resonance imaging. It is anticipated that this distraction will reduce the anxiety experienced during magnetic resonance imaging and thus reduce the tendency of the patient to move. The imaging done with a MRI apparatus should therefore be more efficient.

The present invention can transfer any active optical image across any magnetic flux gradient that separates a region having a high magnetic flux density from a region having a low magnetic flux density. This gradient is difficult to cross using coaxial cable due to the electromagnetic interference set up by the change in the magnetic flux density. The interaction between the magnetic field and the light, if measurable, is probably limited to a change in the polarization of the light. Neither the optical or magnetic resonance images will be degraded. The present invention therefore offers a universal image transfer apparatus for transferring entire real time optical images across a magnetic flux gradient and video images into the imaging zone of a MRI system.

DETAILED DESCRIPTION

Figure 1:
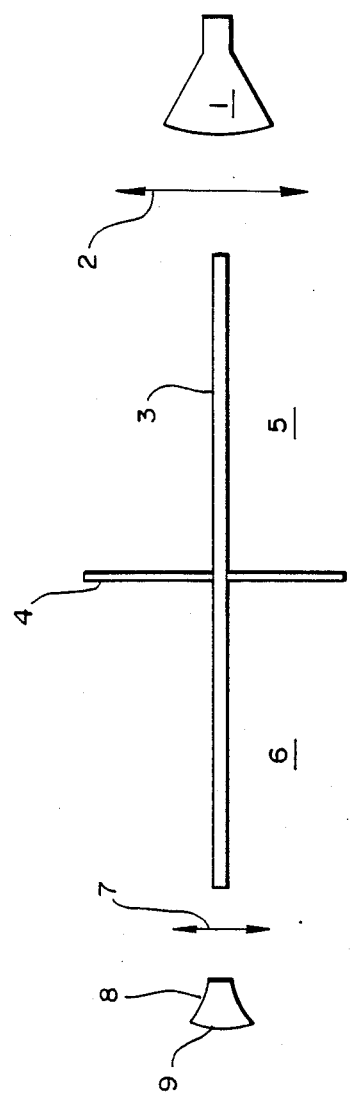
FIG. 1 shows an embodiment of the present invention that uses a coherent fiberoptic bundle to project an image from a high intensity CRT that is located in a region of low magnetic flux density into a region having a high magnetic flux density such as the imaging zone of a MRI system.

FIG. 1 shows an embodiment of the present invention that uses a coherent fiberoptic bundle to transfer a video image across a magnetic flux gradient into a region having a high magnetic flux density such as encountered in the imaging zone of a MRI system. Transfer optics 2, illustrated symbolically by a double arrow, direct the image formed by a high intensity CRT 1 into a coherent fiberoptic bundle 3. The CRT may comprise, for example, the projector for a large screen television of a type that is known in the art. The high intensity CRT provides an input that is very bright so as to compensate for attenuation of the image in the fiberoptic bundle. The transfer optics, coherent fiberoptic bundle and fiberoptic taper are likewise are well known in the art.

The coherent fiberoptic bundle 3 crosses magnetic flux gradient 4 that separates regions 5 and 6. Gradient 4 can be formed from any of several known magnetic shields of the type typically used to attenuate the magnetic field of the MRI system. Region 5 can comprise the control room and region 6 the imaging zone of any MRI system.

Transfer optics 7, illustrated symbolically by a double arrow, transfer the image emerging from fiberoptic bundle 3 to fiberoptic taper 8. The transfer optics and fiberoptic taper are well known in the art. The patient views the image by viewing the expanded end 9 of fiberoptic taper 8.

Figure 2:
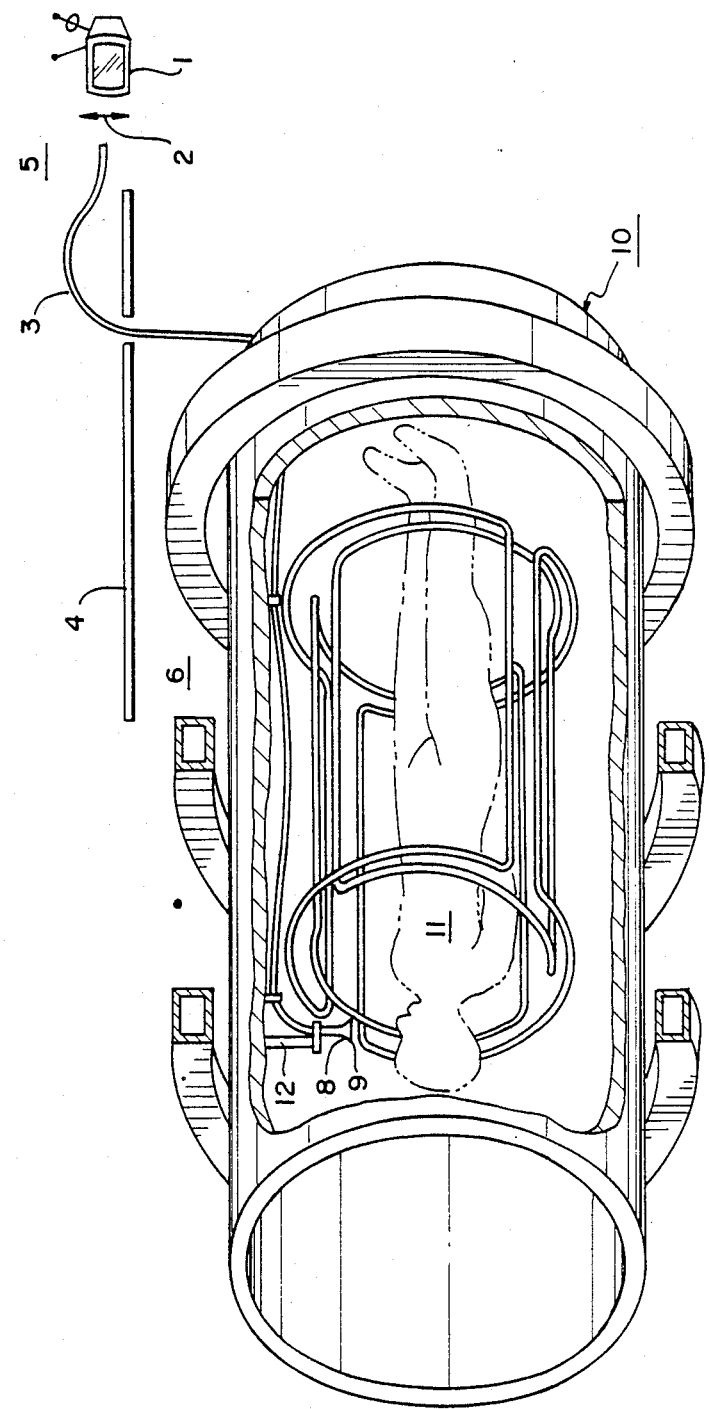
FIG. 2 illustrates the use of the present invention with a MRI system.

FIG. 2 illustrates how the present invention would be used in the imaging zone of an MRI apparatus 10, many examples of which are known in the art. The high intensity CRT 1 is positioned in region 5 corresponding to a region of low magnetic flux density outside of the gradient created by magnetic shield 4. The CRT could be located in the control room for the MRI apparatus. The fiberoptic taper 8 should be positioned so that the patient 11 can see the image emerging from expanded end 9. Nonmetal mounting bracket 12 positions the fiberoptic taper 8. The mounting bracket should be adapted to the needs of each MRI apparatus and measurement. The design of an appropriate mounting bracket is considered to be within the ability of one skilled in the art.

The coherent fiberoptic bundle 3 is preferred at present for transferring the image into the imaging zone of the MRI apparatus. The orientation of the patient needed for proper magnetic resonance imagining cannot be assumed to promote proper display of a video image. The space available in the imaging zone of the MRI apparatus is generally too small to permit the video image to be transferred directly to the patient along a line of sight path for every orientation of the patient. A fiberoptic bundle is easier to bend as needed. The fiberoptic bundle also should simplify the task of positioning the fiberoptic taper within the field of view of the patient for each measurement since the orientation of the patient in the imaging zone is not constant.

Finally, the fiberoptic bundle should require a smaller hole in the magnetic shield. Reducing the size of the hole using conventional transfer optics would require the awkward step of reducing the image or focusing the reduced image at the plane of the shield since a large hole would allow the magnetic flux to leak out and disrupt the CRT.

The foregoing advantages of a fiberoptic bundle make it the preferred means for transferring the video image across the magnetic flux gradient. Transfer optics comprising elements such as mirrors and lenses nevertheless could be used to project the video image into the imaging zone and are therefore considered an alternative to a fiberoptic bundle.

The use of a fiberoptic bundle made from silica or plastic fibers costs less. Fiberoptic bundles made of silica fibers are known that have a smaller diameter than comparable fiberoptic bundles made of plastic fibers. A fiberoptic bundle of silica fibers would require a smaller hole in the magnetic shield which is desirable. A coherent fiberoptic bundle formed from fibers of fused quartz is more expensive but also attenuates less light so that a lower intensity CRT could generate the video image. A fused quartz fiberoptic bundle could transfer an optical image out of the imaging zone if the image was not brightly illuminated. High intensity lighting in the imaging zone of an MIR system is not desirable since it would bother the eyes of the patient. A coherent fiberoptic bundle made of fused quartz could thus allow a doctor to view the patient during magnetic resonance imaging.

It is to be appreciated that the image that is displayed to the patient should be chosen to reduce anxiety. The selection of an appropriate video program is considered to be within the ability of one skilled in the art.

The principles preferred embodiments and modes of operation of the present invention have been set forth in the foregoing specification. The invention, however, should not be viewed as limited to the particular embodiment shown since it is intended merely to illustrate the invention. Variations and changes may be made by those skilled in the art without departing from the scope and spirit of the invention set forth in the appended claims.

What is claimed is:

1. A video display for an imaging zone of a Magnetic Resonance Imaging (MRI) apparatus, comprising:
   means for receiving a video image;
   means for transferring the video image into the imaging zone of the MRI apparatus when the MRI apparatus is generating a high magnetic flux density in the imaging zone without the high magnetic flux density degrading the video image or the video image degrading the high magnetic flux density; and
   means for displaying the video image to a patient who is in the imaging zone when the MRI apparatus is generating the high magnetic flux density in the imaging zone.

2. A video display as claimed in claim 1, wherein:
   the video image comprises the image formed on a cathode ray tube (CRT);
   the transfer means comprises a coherent fiberoptic bundle; and
   the display means comprises a fiberoptic display.

3. A video display as claimed in claim 2, wherein: the CRT generates a high intensity image;
   the coherent fiberoptic cable comprises silica optical fibers; and
   the fiberoptic display comprises a fiberoptic taper.

4. A video display as claimed in claim 3, wherein the display means further comprises means for positioning the fiberoptic taper so that a patient in the imaging zone can see the video image.

5. An apparatus for transferring an active optical image across a gradient between a region having a high magnetic flux density and a region having a low magnetic flux density, comprising:
   means for receiving the entire active optical image in one region in real time;
   means for transferring the entire active optical image across the gradient together in real time without the magnetic flux degrading the image or the image degrading the magnetic flux; and
   means for displaying the entire active optical image in the other region in real time.

6. An apparatus as claimed in claim 5, wherein:
   the region of high magnetic flux density is an imaging zone of a magnetic resonance imaging (MRI) apparatus;
   the means for receiving the entire active optical image is located in the region of low magnetic flux density; and
   the means for displaying the entire active optical image is located in the imaging zone.

7. An apparatus as claimed in claim 6, wherein:
   the means for receiving the entire active optical image comprises means for receiving a video image from a CRT;
   the means for transferring the entire active optical image together in real time comprises a coherent fiberoptic bundle; and
   the means for displaying the entire active optical image in real time comprises a fiberoptic display.

8. An apparatus as claimed in claim 5, wherein the means for transferring the optical image comprises a fiberoptic bundle.

9. An apparatus as claimed in claim 8, wherein the fiberoptic bundle is coherent.

10. An apparatus as claimed in claim 8, wherein:
    the means for receiving the entire active optical image is located in a region having a low magnetic flux density; and
    the means for displaying the entire active optical image is located in a region having a high magnetic flux density.

11. A method of displaying a video image in an imaging zone of a Magnetic Resonance Imaging (MRI) apparatus, comprising the steps:
    receiving the video image;
    transferring the video image into the imaging zone of the MRI apparatus when the MRI apparatus is generating a high magnetic flux density in the imaging zone without the high magnetic flux density degrading the video image or the video image degrading the high magnetic flux density; and
    displaying the video image to a patient who is in the imaging zone when the MRI apparatus is generating the high magnetic flux density in the imaging zone.

12. A method of transferring an entire active optical image across a gradient between a region having a high magnetic flux density and a region having a low magnetic flux density, comprising the steps of:

receiving the entire active optical image in one region;

transferring the entire active optical image across the gradient together in real time without the magnetic flux degrading the image or the image degrading the magnetic flux; and displaying the entire active optical image in the other region in real time.

13. A method as claimed in claim 12, wherein the step of receiving the active image comprises the step of dividing the active image among the individual fibers of a fiberoptic cable.

14. A method as claimed in claim 12, wherein:

the step of receiving the entire active optical image is performed in the region of low magnetic flux density; and the step of displaying the entire active optical image in real time is performed in the region of high magnetic flux density.

15. A method as claimed in claim 14, wherein the region of high magnetic flux density is an imaging zone of an MRI system.

16. A Magnetic Resonance Imaging (MRI) apparatus, comprising:

means for receiving a video image;

means for transferring the video image into an imaging zone of the MRI apparatus when the MRI apparatus is generating a high magnetic flux density in the imaging zone without the high magnetic flux density degrading the video image or the video image degrading the high magnetic flux density; and means for displaying the video image to a patient who is in the imaging zone when the MRI apparatus is generating the high magnetic flux density in the imaging zone.

17. A MRI apparatus as claimed in claim 16 wherein:

the video image comprises the image formed on a cathode ray tube (CRT);

the transfer means comprises a coherent fiberoptic bundle; and the display means comprises a fiberoptic display.

18. A MRI apparatus as claimed in claim 17 wherein:

the CRT generates high intensity image;

the coherent fiberoptic cable comprises silica optical fibers; and the fiberoptic display comprises a fiberoptic taper.

19. A MRI apparatus as claimed in claim 18, wherein the display means further comprises means for positioning the fiberoptic taper so that a patient in the imaging zone can see the video image.

20. An apparatus for transferring an optical image across a gradient between a region having a high magnetic flux density and a region having a low magnetic flux density, comprising:

means for receiving the optical image in a region of low magnetic flux density;

means for transferring the optical image across the gradient without the magnetic flux degrading the image or the image degrading the magnetic flux; and means for displaying the optical image in having a high magnetic flux density, wherein the region of high magnetic flux density is an imaging zone of a magnetic resonance (MRI) apparatus.

21. An apparatus as claimed in claim 20, wherein:

the means for receiving the optical image comprises means for receiving a video image from a CRT;

the means for transferring the optical image comprises a coherent fiberoptic bundle; and the means for displaying the optical image comprises a fiberoptic display.

22. A method of transferring an optical image across a gradient between a region having a high magnetic flux density and a region having a low magnetic flux density, comprising the steps of:

receiving the optical image in a region of low magnetic flux density;

transferring the optical image across the gradient without the magnetic flux degrading the image or the image degrading the magnetic flux; and displaying the optical image in the region of high magnetic flux density corresponding to an imaging zone of an MRI apparatus.

* * * * *